(12) United States Patent
Niwa et al.

(10) Patent No.: US 9,002,075 B2
(45) Date of Patent: Apr. 7, 2015

(54) INTERPRETATION SUPPORT SYSTEM

(75) Inventors: Kenichi Niwa, Otawara (JP); Maki Minakuchi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1476 days.

(21) Appl. No.: 12/061,340

(22) Filed: Apr. 2, 2008

(65) Prior Publication Data

US 2008/0249807 A1    Oct. 9, 2008

(30) Foreign Application Priority Data

Apr. 3, 2007  (JP) ................................. 2007-097123

(51) Int. Cl.
*G06K 9/00* (2006.01)
*G06F 19/00* (2011.01)
*G06Q 50/24* (2012.01)

(52) U.S. Cl.
CPC .............. *G06F 19/321* (2013.01); *G06Q 50/24* (2013.01)

(58) Field of Classification Search
CPC ....................................................... G06K 9/00
USPC .............................................................. 705/3
See application file for complete search history.

(56) References Cited

U.S. PATENT DOCUMENTS 5,655,084 A * 8/1997 Pinsky et al. ...................... 705/3
5,807,256 A * 9/1998 Taguchi et al. ................ 600/425
2001/0051881 A1 * 12/2001 Filler ................................. 705/3
2005/0108060 A1 * 5/2005 Sasano .............................. 705/3
2008/0215525 A1 * 9/2008 Kakimoto et al. ................ 707/1

FOREIGN PATENT DOCUMENTS

JP    2004-305551    11/2004
JP    2006-268075    10/2006

OTHER PUBLICATIONS

U.S. Appl. No. 12/246,117, filed Oct. 6, 2008, Yamagishi, et al.

* cited by examiner

*Primary Examiner* — Michael Fuelling
(74) *Attorney, Agent, or Firm* — Oblon, McClelland, Maier & Neustadt, L.L.P.

(57) ABSTRACT

A medical image storage unit stores medical image. A medical image observation terminal adds interpretation information for medical image and the creator name for interpretation information to the supplementary information of medical image. A reference terminal obtains medical image from the medical image storage unit in order to display medical image. An evaluation management unit instructs the reference terminal to display an evaluation input screen for medical image to allow an evaluation to be entered if the interpretation information has been added to the supplementary information of medical image obtained in the reference terminal, and it then adds evaluation to the supplementary information of medical image stored in the medical image storage unit after receiving an input from the reference terminal and transmits evaluation to the destination for the evaluation that corresponds to the creator name added to the supplementary information of medical image.

8 Claims, 6 Drawing Sheets

FIG. 2

| CREATOR NAMES | ENCRYPTION | CORRESPONDING DESTINATIONS OF EVALUATIONS |
|---|---|---|
| Dr.A | | Dr.A@hospitalA.com |
| Dr.B | PRESENT(123) | ALLDR@hospitalB.com |
| ENGINEER A | | gishiA@hospitalC.com |
| ... | ... | ... |

FIG. 3

INTERPRETATION SUPPORT SYSTEM

BACKGROUND OF THE INVENTION

1. Field of the Invention

The present invention relates to an interpretation support system for evaluating interpretation reports of medical images and for transmitting said evaluations to a predetermined address.

2. Description of the Related Art

In recent years, medical diagnostic apparatuses have been used to collect information about the inside of a subject and convert the inside of the subject into an image according to the collected information to create a medical image. Examples of such medical diagnostic apparatuses include ultrasonic diagnostic apparatuses, X-ray apparatuses, MRI apparatuses (nuclear magnetic resonance imaging diagnostic apparatuses), and PET apparatuses (nuclear medicine diagnostic apparatuses).

Additionally, there are also image servers for storing the medical images created by such medical diagnostic apparatuses. There are also report servers that allow radiologists to retrieve a medical image from said image server, display the medical image, perform interpretation of the medical image through measurements and analysis, create an interpretation report, and then record the report in association with the corresponding medical image.

The interpretation support system comprises the abovementioned image server and report server and other parts. A medical image as referred to herein is one that conforms to standards such as DICOM (Digital Imaging and Communications in Medicine) and that includes supplementary information such as patient information along with image information.

A physician who makes a request to a radiologist for interpretation (hereinafter referred to as "requesting physician") refers to the interpretation report for a specific patient created by the radiologist along with the corresponding medical image and also uses other information about said patient, such as interview results, to comprehensively judge the medical image and conduct diagnosis of said patient.

Conventional systems have been proposed to transmit an evaluation of an interpretation report to an interpretation center, in order to select a radiologist suited to the details of the examination, in consideration of status information and qualitative evaluations of the radiologists (for example, Japanese Unexamined Patent Application Publication No. 2006-268075).

Conventional interpretation support systems for medical images are capable of conducting diagnoses efficiently by referring to an interpretation report if using an interpretation report system or referring to comments and annotations such as arrows attached to the medical image if no interpretation report system is being used. However, even in a system that comprises such an interpretation report system, the requesting physician does not provide the radiologist with any evaluation of, for example, the usefulness of the interpretation of the medical image being used. In this case, if the radiologist wishes to check the quality of their own interpretation to help improve the quality of future interpretations, they would have to ask the relevant requesting physician or other party about their evaluation of the medical image. Therefore, it has been difficult in the prior art for a radiologist to receive evaluations of their own interpretations with only the medical image.

SUMMARY OF THE INVENTION

The present invention has been developed in view of the situations mentioned above and is directed to provide an interpretation support system in which evaluations of interpretation information such as comments and annotations made on a medical image can be received by the person who has created said interpretation information, using the medical image.

The first embodiment of the present invention will now be described. A medical image storage unit stores a medical image, including supplementary information such as patient information and image information, as well as interpretation information such as comments or annotations made for said medical image. An evaluation management unit receives inputs of an evaluation of the interpretation information and adds said evaluation to the supplementary information. The first embodiment of the present invention is an interpretation support system that comprises the abovementioned configurations.

According to the first embodiment, an evaluation of the interpretation of the medical image is added as supplementary information. This enables the evaluation of the interpretation of the medical image to be received simply by referring to the medical image.

The second embodiment of the present invention will now be described. A medical image storage unit stores a medical image, including supplementary information such as patient information and image information, as well as information related to said medical image. An interpretation report storage unit stores an interpretation report that contains the results of a interpretation of the medical image. An evaluation management unit receives inputs of an evaluation of the interpretation report and adds said evaluation to the supplementary information of the medical image, where the information for specifying the storage destination is added to said interpretation report. The second embodiment of the present invention is an interpretation support system that comprises the abovementioned configuration.

According to the second embodiment, an evaluation of the interpretation report of the medical image is added as supplementary information to the medical image in which the location can be specified from that interpretation report. This enables the evaluation of the interpretation of the medical image to be received simply by referring to the medical image.

In the third embodiment of the present invention, a medical image storage unit stores a medical image, including supplementary information such as patient information along with image information that has been captured by a medical image-capturing device. A medical image observation terminal adds interpretation information, such as comments or annotations for said medical image, and the name of the creator of said interpretation information to the supplementary information. A reference terminal obtains the medical image from the medical image storage unit after receiving an instruction to do so from an operator and then displays the medical image. An evaluation management unit instructs the reference terminal to display an evaluation input screen for said medical image to allow an evaluation to be entered if the interpretation information has been added to the supplementary information obtained in the reference terminal, then adds said evaluation or said storage destination of the evaluation to the supplementary information of said medical image stored in the medical image storage unit after receiving an input from the reference terminal, and then transmits a report regarding said evaluation to the destination of the evaluation that corresponds to the name of the creator added to said supplementary information. The third embodiment of the present invention is an interpretation support system that comprises the abovementioned configuration.

According to the third embodiment, an evaluation of the interpretation information is added to the supplementary information of the medical image, while the evaluation of the interpretation information or evaluation-related information is transmitted to the destination of the evaluation that corresponds to the creator name added to the supplementary information. Accordingly, the radiologist who created the interpretation can easily receive the evaluation of the interpretation information.

DETAILED DESCRIPTION OF THE EMBODIMENTS

[First Embodiment]

Figure 1:
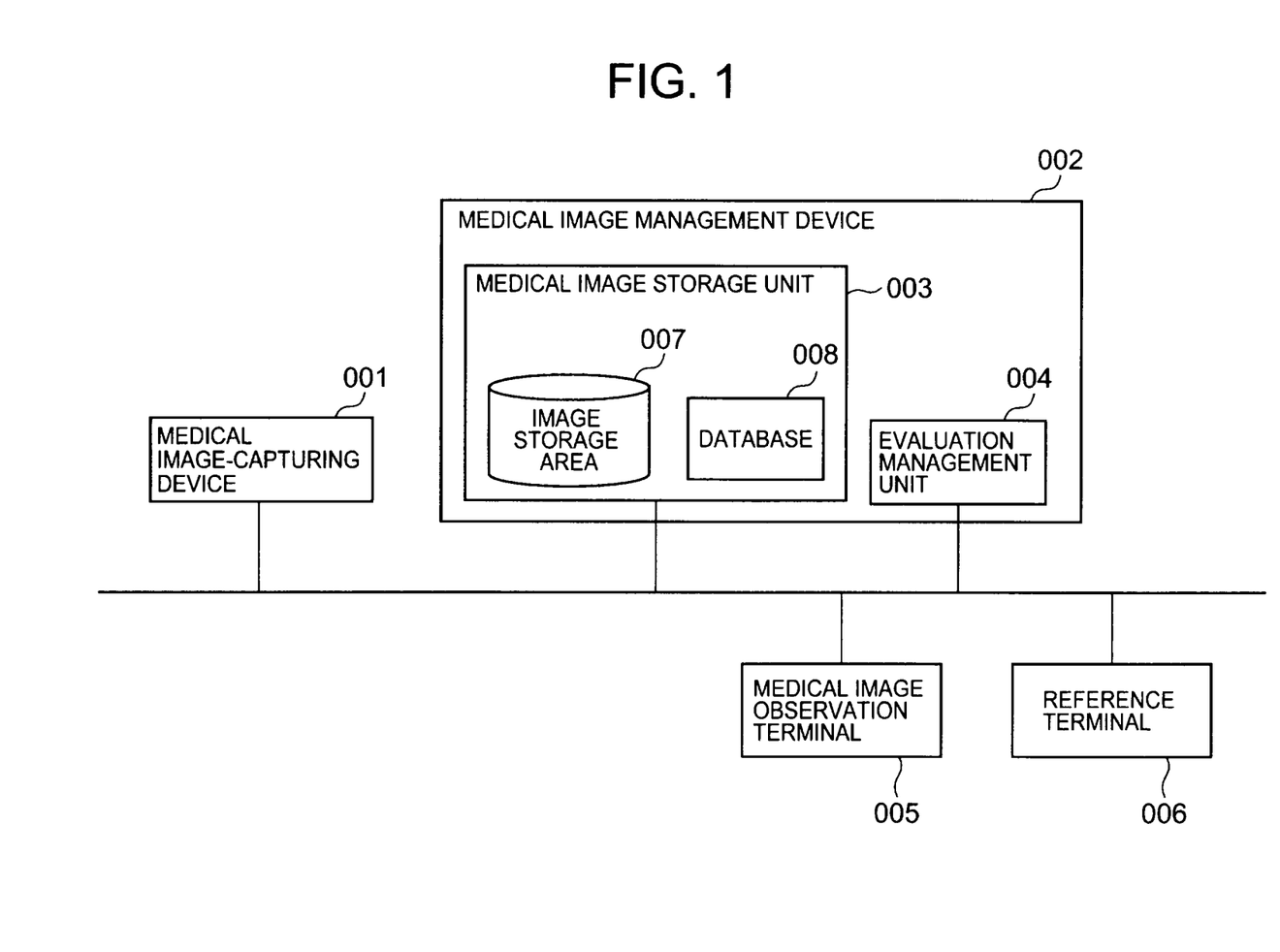
FIG. 1 is a block diagram of an interpretation support system according to the first embodiment.

An interpretation support system according to the first embodiment of the present invention will now be described. FIG. 1 is a block diagram of an interpretation support system according to this embodiment. As shown in FIG. 1, a medical image-capturing device 001, a medical image management device 002, a medical image observation terminal 005, and a reference terminal 006 are all connected via a network. Thus, each device is capable of communicating with each other. A medical image as referred to in the following descriptions is one that conforms to, for example, DICOM standards and includes supplementary information such as patient information along with image information.

The medical image-capturing device 001 is of a modality such as an X-ray apparatus, a CT apparatus, an MRI apparatus, or an ultrasonic diagnostic apparatus. A medical image of the subject captured by the medical image-capturing device 001 is transmitted in DICOM format from the medical image-capturing device 001 to the medical image management device 002.

The medical image management device 002 comprises a medical image storage unit 003 and an evaluation management unit 004. The medical image storage unit 003 includes an image storage area 007 and a database 008. In this embodiment, the medical image storage unit 003 and the evaluation management unit 004 are included in a single device, but they can also be placed in separate devices.

The medical image storage unit 003 receives the medical image from the medical image-capturing device 001 and stores it in the image storage area 007. The medical image storage unit 003 also registers the information that is attached to the medical image, such as patient information (e.g., patient ID) and the image UID (unique ID), in the database 008.

The medical image storage unit 003 receives a request from the medical image observation terminal 005 and transmits the medical image corresponding to the request to the medical image observation terminal 005.

The medical image storage unit 003 receives from the medical image observation terminal 005 a medical image in which interpretation information including comments and annotations such as arrows (hereinafter referred to as "annotations") for a stored medical image has been added to the supplementary information along with the name of the person creating said interpretation information, and then updates the corresponding medical image that has been stored in the medical image storage area 007. The medical image storage unit 003 also registers the comments and comments UID and the annotations and annotations UID (the comments UID and annotations UID are hereinafter correctively referred to as "interpretation information UID") into the database 008 along with the name of the person who created the interpretation information that has been added to the supplementary information of said medical image.

The medical image storage unit 003 receives a request to transmit a medical image based on an instruction from a requesting physician through the reference terminal 006 and transmits to the reference terminal 006 the medical image that corresponds to the request. At the same time, the medical image storage unit 003 searches for the interpretation information UID in the database 008 and determines from the presence thereof if the interpretation information has been added to the supplementary information of the medical image that has been transmitted. If the interpretation information has been added to the supplementary information, the medical image storage unit 003 will report to the evaluation management unit 004 information indicating that the interpretation information has been added to the supplementary information of the medical image that has been transmitted to the reference terminal 006.

Figure 2:
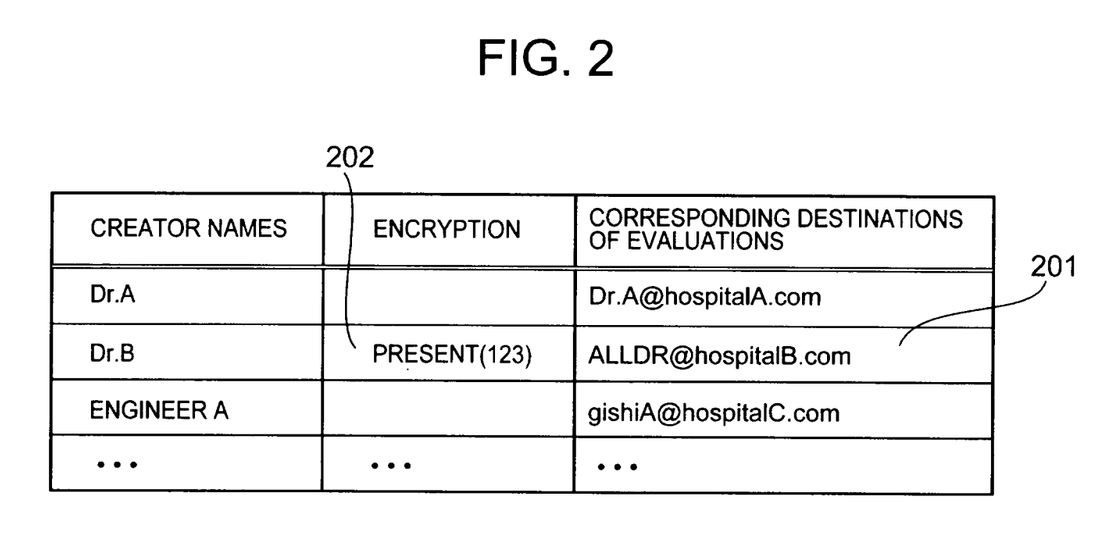
FIG. 2 illustrates an example of a table including creator names and the corresponding destinations of evaluations.

The evaluation management unit 004 comprises a CPU and a memory area. The evaluation management unit 004 preliminarily records a table, as shown in FIG. 2, that shows the names of the creators of the interpretation information and the corresponding destinations of the evaluations (for example, the email addresses of the creators). FIG. 2 is a table illustrating the creator names and the corresponding destinations of the evaluations.

Figure 3:
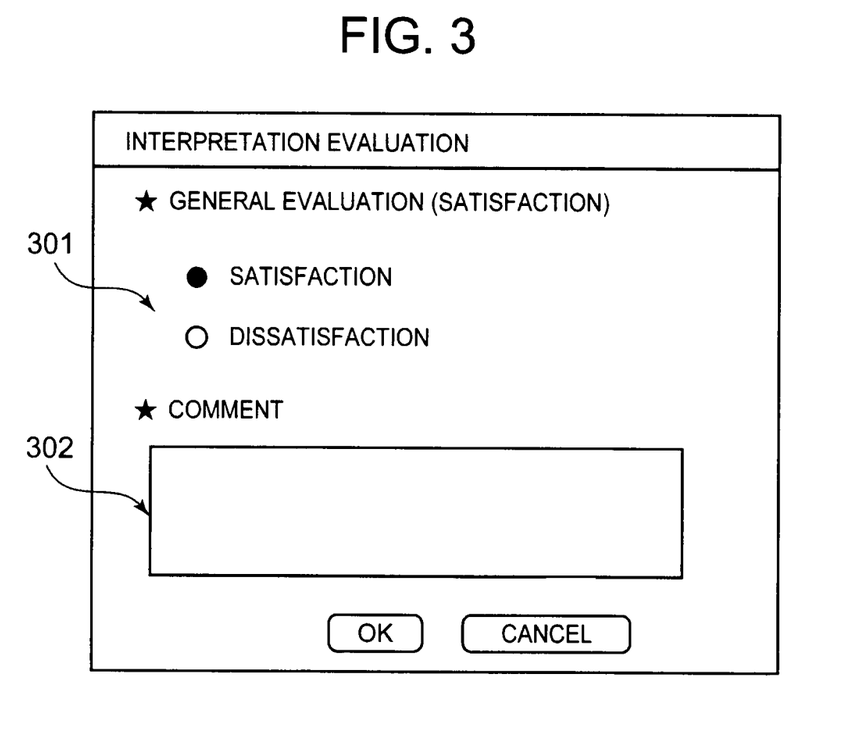
FIG. 3 illustrates an example of an evaluation input screen.

After receiving the information indicating that the interpretation information has been added to the supplementary information along with the information about the reference terminal 006 of the destination for transmitting the medical image, the evaluation management unit 004 instructs the reference terminal 006 to display an evaluation input screen as shown in FIG. 3 with respect to the medical image transmitted from the medical image storage unit 003. FIG. 3 illustrates an example of a screen used for entering an evaluation of the interpretation information. In this embodiment, the screen as described herein includes a radio button 301 and a comment field 302, as shown in FIG. 3, by which an evaluation level is entered in the evaluation screen to allow for a detailed understanding of the evaluation made by the requesting physician. However, the method for entering this evaluation is not specially limited to any one type. For example, the button 301 may be used by itself if only the evaluation level is to be obtained. Additionally, in this embodiment, an evaluation is entered for each medical image. These evaluations may be entered for each item of interpretation information, such as each comment.

As described herein, in this embodiment, the evaluation management unit 004 receives from the reference terminal 006 the information indicating that the interpretation information has been added to the supplementary information.

Meanwhile, the evaluation management unit 004 can analyze the medical image transmitted from the reference terminal 006 and check for the presence of the interpretation information, in order to thereafter determine if the interpretation information has been added to the supplementary information of said medical image.

The evaluation management unit 004 receives from the reference terminal 006 the inputs for the evaluation of the medical image, and adds said evaluation to the supplementary information of the corresponding medical image that is stored in the medical image storage unit 003.

As described herein, in this embodiment, the evaluation management unit 004 adds the evaluation itself to the supplementary information of the medical image. However, as alternatives to this configuration of adding the evaluation itself directly into the supplementary information, the evaluation management unit 004 can be configured to create a file of evaluations that have been entered (the file is herein referred to as "1.2.128.xxx.hyouka.inf") and store that file in a predetermined storage location (e.g., the same server for storing the medical image, but even if it is stored in a different server, that different server can be specified in the information regarding storage destination) and add information regarding the storage destination of that file (e.g., ¥¥192.168.0.1¥share¥1.2.128.xxx.hyouka.inf) to the supplementary information of the medical image. This enables the user referring to the medical image to obtain the evaluation of said medical image according to the information regarding the storage destination of the evaluation file that has been added to the supplementary information of that medical image. Herein, the evaluation management unit 004 can be placed on an interpretation report terminal or the reference terminal 006. In this case, a report client or an image viewer on the interpretation terminal or an HIS client on the reference terminal 006 will create the abovementioned evaluation file and add the storage destination thereof to the supplementary information of the medical image.

Additionally, in this embodiment, the evaluation management unit 004 adds only the evaluation to the supplementary information of the medical image. Conversely, it may add information specifying the user who performed the evaluation (e.g., email address) to the supplementary information, together with the evaluation. This facilitates the exchanging of information between the person performing the evaluation and the person being evaluated. Specifically, if the evaluation management unit 004 is placed within the interpretation report terminal or the reference terminal 006, this will be performed by the report client or the image viewer on the interpretation terminal or the HIS client on the reference terminal 006.

Moreover, the evaluation management unit 004 searches the database 008 in the medical image storage unit 003 to extract the name of the creator of the interpretation information that has been evaluated. Then, the evaluation management unit 004 refers to an internal table showing the creator names and each corresponding destination for the evaluation. The evaluation management unit 004 then extracts the destination for the evaluation corresponding to the creator being searched for.

The evaluation management unit 004 transmits the evaluation of the interpretation information or evaluation-related information such as a storage destination that are received from the reference terminal 006 to the extracted destination for the evaluation. As described herein, if evaluation-related information such as a storage destination is received, an operator (e.g., a radiologist) can obtain the evaluation of the interpretation information they created by referring to the evaluation based on that information.

An example case will be described below in which an evaluation has been performed through the reference terminal 006 with respect to the interpretation information created by "Dr. A." The evaluation management unit 004 searches the database 008 to extract Dr. A, who is the creator of the evaluated interpretation information. The evaluation management unit 004 then refers to the table shown in FIG. 2 to extract the destination of the evaluation corresponding to Dr. A (i.e., "Dr.A@hospital.com"). The evaluation management unit 004 then transmits the evaluation received from the reference terminal 006 to Dr.A@hospital.com.

In cases in which the evaluation can be entered in the evaluation input screen for each item of interpretation information as described earlier, the destination for the evaluation will be extracted for each item of interpretation information. This makes it possible to transmit the evaluation of the interpretation information to the destinations for the evaluation extracted for each item of interpretation information.

Additionally, in this embodiment, it is possible to encrypt the destination for the evaluation. For example, the destination for the evaluation for "Dr. B" shown in FIG. 2 is encrypted. Specifically, as shown in FIG. 2, a hospital mail server ("ALLDR@hospitalB.com" shown in FIG. 2) or the like is specified as the destination for the evaluation 201, and encryption information 202 is also listed on the table. In this case, as described above, when the evaluation management unit 004 determines that the creator of the interpretation information corresponding to the evaluation received from the reference terminal 006 is "Dr. B", the evaluation management unit 004 will transmit the evaluation corresponding to the interpretation information to the hospital mail server that is the destination for the evaluation 201. Additionally, the evaluation management unit 004 transmits the encryption information 202 to the destination of the evaluation 201. Once this information is received, the mail server analyzes the encryption information to determine an actual destination for the evaluation for "Dr. B" and then transfers the evaluation of the interpretation information to the actual destination for the evaluation for Dr. B. This enables the evaluation of the interpretation information to be transmitted to the creator of that interpretation information without disclosing the identification of the creator to the requesting physician if the creator wishes not to be acknowledged by other persons, such as when a medical image is being used outside the relevant medical facilities.

Moreover, in this embodiment, the evaluation management unit 004 includes a table of the destinations for the evaluations corresponding to each creator name, and thereby the destinations for the evaluations are extracted with reference to the table according to the creator name added to the supplementary information. Conversely, the destination for the evaluation corresponding to the creator name can be added when the operator adds the creator name to the supplementary information of the medical image through the medical image observation terminal 005. The evaluation management unit 004 may then transmit the evaluation to the destination for the evaluation added to the supplementary information of the medical image. This enables the destination for the evaluation to be changed depending on the radiologist receiving the evaluation.

Furthermore, in this embodiment, taking into consideration network loads, only the evaluation corresponding to the interpretation information is transmitted. Conversely, a medical image in which the evaluation is added to the supplementary information may be transmitted as the evaluation to the destination for the evaluation in order to make clear which medical image has been evaluated against each interpretation information.

The medical image observation terminal 005 is an information terminal comprising a CPU, examples of which include a PC (personal computer). This medical image observation terminal 005 is equivalent to the "destination management unit" according to Claim 3.

The medical image observation terminal 005 sends a request to the medical image management device 002 for the medical image upon the instruction of a radiologist. The medical image observation terminal 005 then displays the medical image that has been received from the medical image management device 002.

The medical image observation terminal 005 adds the interpretation information and the name of the creator of said interpretation information to the supplementary information of the displayed medical image according to the input of the radiologist. The medical image observation terminal 005 also transmits the medical image, in which the interpretation information and the creator name have been added to the supplementary information, to the medical image management device 002.

The reference terminal 006 is an information terminal comprising a CPU, examples of which include a PC (personal computer).

The reference terminal 006 sends a request to the medical image management device 002 for the medical image upon the instruction of a requesting physician. The reference terminal 006 displays the medical image received from the medical image management device 002 in accordance with the request.

Additionally, the reference terminal 006 displays the evaluation input screen as shown in FIG. 3, which has been transmitted from the evaluation management unit 004.

The reference terminal 006 transmits the information regarding the evaluation level specified through the radio button 301 as well as comments made through the comment field 302, which are shown in FIG. 3, to the evaluation management unit 004 in accordance with the input of the requesting physician.

Figure 4:
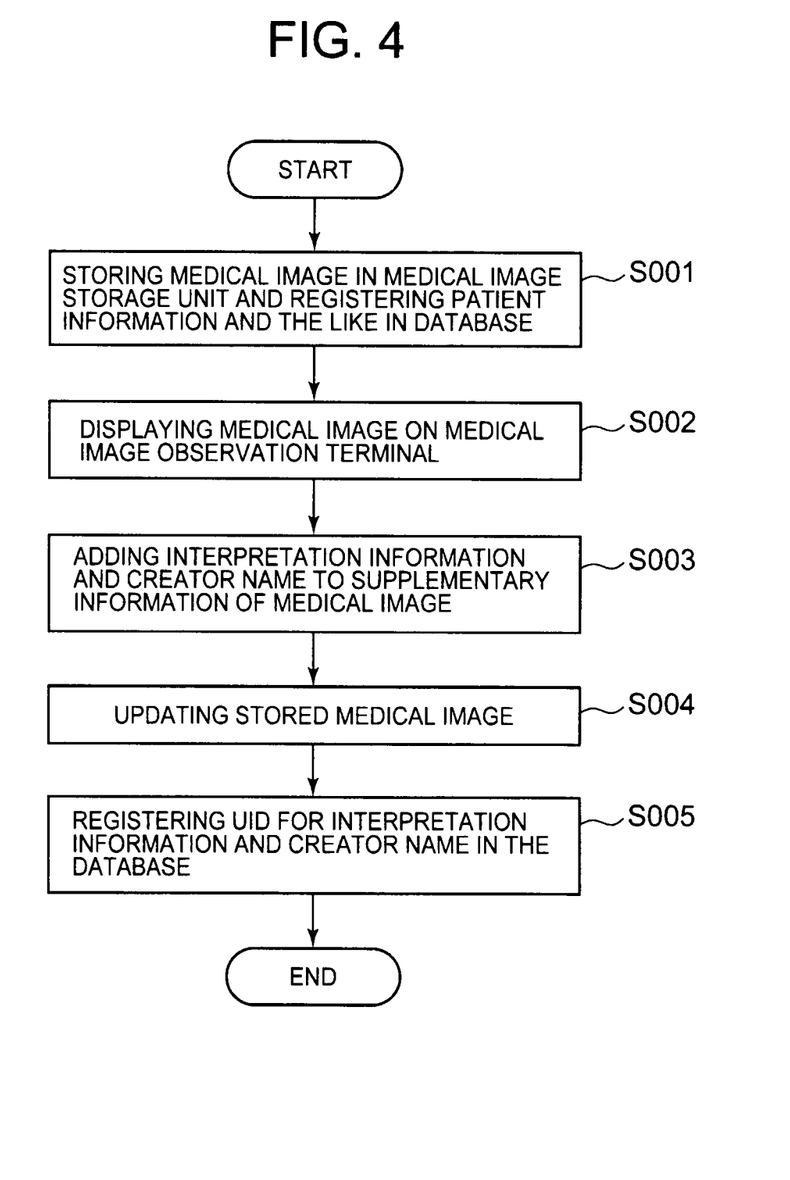
FIG. 4 is a flowchart showing a process of adding interpretation information and creator name to the supplementary information of a medical image in an interpretation support system according to the first embodiment.

Turning to FIG. 4, a process of adding the interpretation information and the creator name to the supplementary information of the medical image for an interpretation support system according to this embodiment will now be described. FIG. 4 is a flowchart showing a process of adding the interpretation information and the creator name to the supplementary information of the medical image in an interpretation support system according to this embodiment.

Step S001: The medical image management device 002 stores, in the image storage area 007 of the medical image storage unit 003, a medical image created in the medical image-capturing device 001. The medical image management device 002 also registers patient information and the like in the database 008 of the medical image storage unit 003.

Step S002: After receiving from the medical image observation terminal 005 a request for the medical image based on an instruction from a radiologist, the medical image management device 002 transmits the medical image to the medical image observation terminal 005. The medical image observation terminal 005 displays the received medical image.

Step S003: After receiving inputs from the radiologist, the medical image observation terminal 005 adds the interpretation information such as comments as well as creator name to the supplementary information of the displayed medical image.

Step S004: The medical image observation terminal 005 transmits the medical image, in which the interpretation information and creator name are added to the supplementary information, to the medical image storage unit 003 to update the corresponding medical image stored in the image storage area 007.

Step S005: The medical image observation terminal 005 transmits the UID for the interpretation information and the creator name to the medical image storage unit 003 to register them in the database 008.

Figure 5:
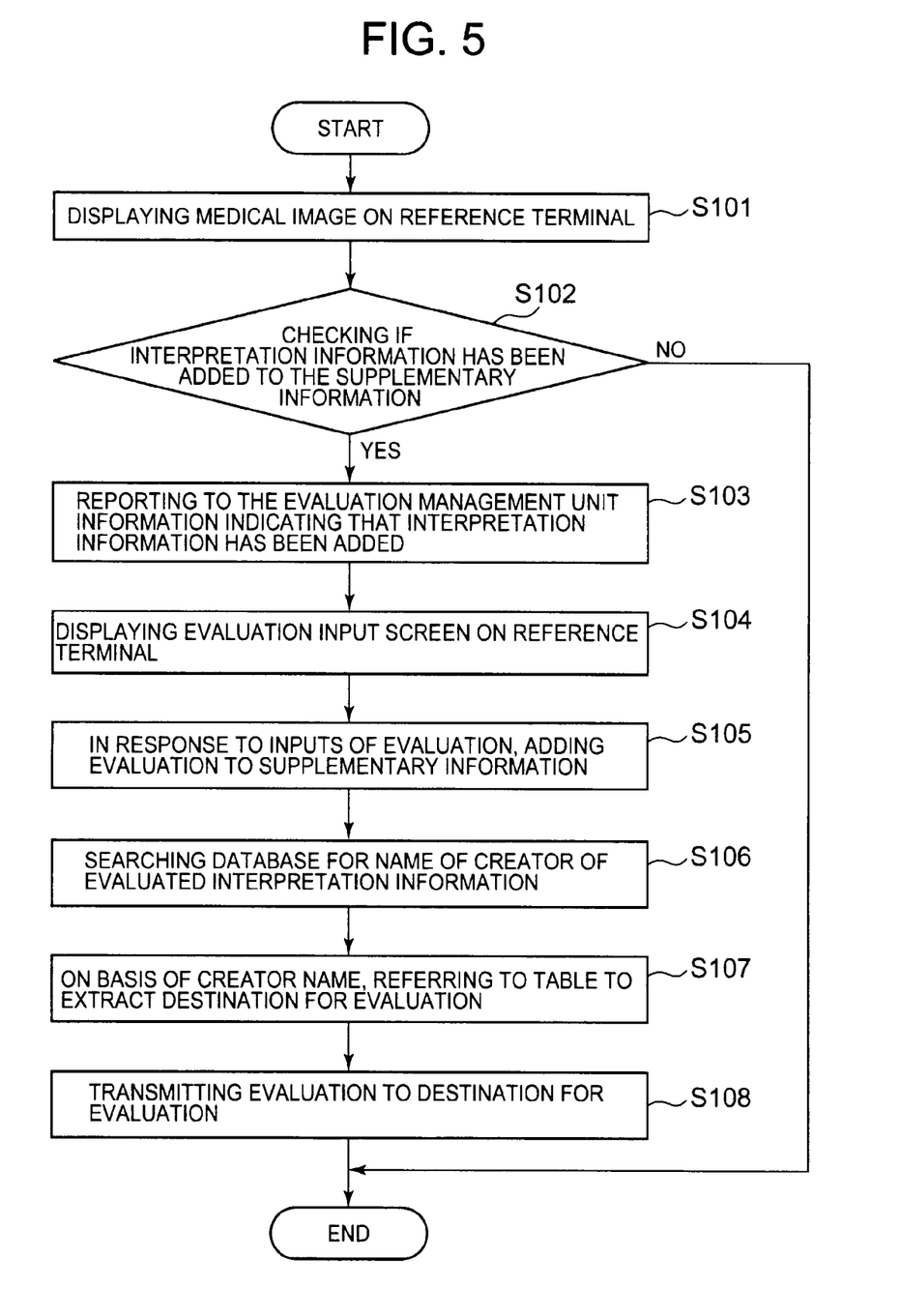
FIG. 5 is a flowchart showing a process of transmitting an evaluation in an interpretation support system according to the first embodiment.

Turning to FIG. 5 a process of transmitting an evaluation for an interpretation system according to this embodiment will now be described. FIG. 5 is a flowchart showing a process of transmitting an evaluation in an interpretation support system according to this embodiment.

Step S101: After receiving from the reference terminal 006 a request for the medical image based on an instruction from a requesting physician, the medical image storage unit 003 transmits the medical image stored in the image storage area 007 to the reference terminal 006. The reference terminal 006 displays the received medical image.

Step S102: The medical image storage unit 003 searches the database 008 to check if the interpretation information has been added to the supplementary information of the medical image displayed in the reference terminal 006. If the interpretation information has been added to the supplementary information, it proceeds to Step S103, whereas if the interpretation information has not been added to the supplementary information, the operation of evaluating the interpretation information will end.

Step S103: The medical image storage unit 003 reports to the evaluation management unit 004 information indicating that the interpretation information has been added to the supplementary information of the medical image displayed in the reference terminal 006.

Step S104: After receiving the report from the medical image storage unit 003, the evaluation management unit 004 instructs the reference terminal 006 to display the evaluation input screen to allow an evaluation to be entered.

Step S105: After receiving the inputs of the evaluation of the interpretation information from the reference terminal 006, the evaluation management unit 004 adds said evaluation to the supplementary information of the corresponding medical image stored in the image storage unit 007.

Step S106: The evaluation management unit 004 searches the database 008 for the name of the creator of the evaluated interpretation information.

Step S107: The evaluation management unit 004, on the basis of the searched name of the creator, refers to an internal table showing the creator names and the corresponding destinations for the evaluation to extract the destination for the evaluation.

Step S108: The evaluation management unit 004 transmits the evaluation or the evaluation-related information regarding the interpretation information, which has been entered from the reference terminal 006 to the destination of the evaluation, to the extracted destination for the evaluation of the creator of the interpretation information.

As described above, an interpretation support system according to this embodiment is capable of adding the evaluation of the interpretation information of the medical image to the supplementary information and transmitting that evaluation to the destination for the evaluation of the creator of the interpretation information. Accordingly, a person referring to the medical image can check the evaluation of the interpretation of the referred medical image. In other words, the creator of the interpretation information can easily obtain the evaluation for that interpretation information. Thus, an interpretation support system according to this embodiment can help to improve the interpretation skills of a radiologist.

Additionally, in this embodiment, the interpretation information, evaluation information, creator names, etc. are registered in a database in order to improve access speed. Conversely, if there is not much need for fast access, it may be configured to obtain each of the abovementioned information from the supplementary information of the medical image.

Additionally, in this embodiment, the evaluation is added to the supplementary information of the image, but it may be organized in another database. Such organization of the evaluations can facilitate statistical processing of the evaluations. Statistical processing is performed for the evaluations and feedback is given to each radiologist, and thereby the reliability of each item of interpretation information can be increased.

[Second Embodiment]

Figure 6:
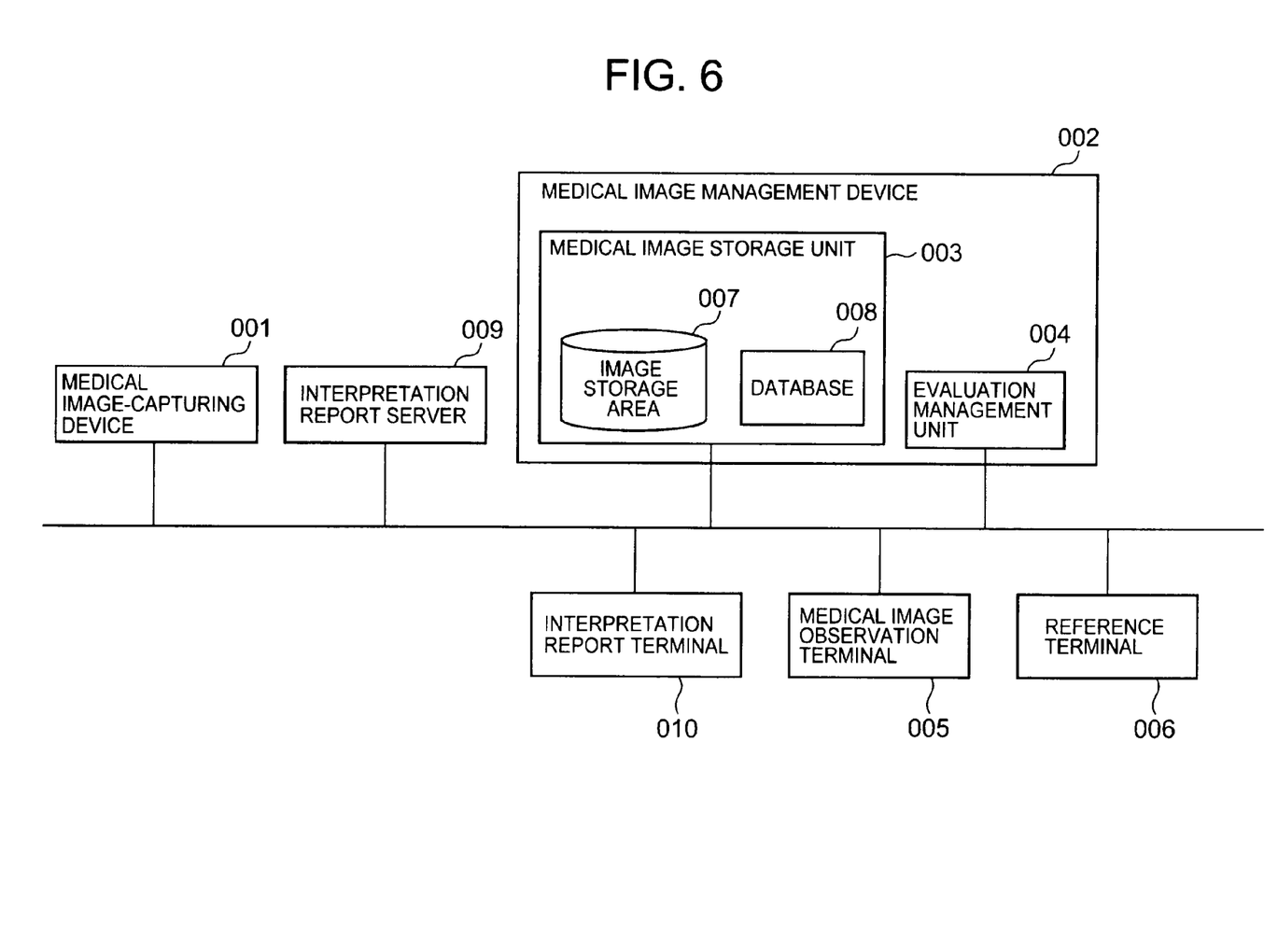
FIG. 6 is a block diagram of an interpretation support system according to the second embodiment.

The second embodiment of the present invention is a system in which an interpretation report system is implemented in an interpretation support system according to the first embodiment. FIG. 6 is a block diagram of an interpretation support system according to this embodiment. In FIG. 6, numerals identical to those in FIG. 1 have the same functions.

Subject to the operation, the medical image storage unit 003 receives medical images from the medical image-capturing device 001 and stores them in the image storage area 007. Additionally, the database 008 of the medical image storage unit 003 registers the information that is attached to the medical image, such as patient information (e.g., patient ID) and image UID.

An interpretation report terminal 010 is an information terminal comprising a CPU, examples of which include a PC (personal computer).

The interpretation report terminal 010 transmits to the medical image storage unit 003 a request for a specific medical image to be transmitted to the medical image observation terminal 005 according to an instruction from a radiologist.

The interpretation report terminal 010 transmits to the interpretation report server 009 the interpretation report that has been created by the radiologist with reference to the medical image displayed in the medical image observation terminal 005.

The medical image observation terminal 005 is an information terminal comprising a CPU, examples of which include a PC (personal computer).

The medical image observation terminal 005 receives the medical image transmitted from the medical image management device 002 according to an instruction from the interpretation report terminal 010 and then displays said medical image.

The medical image observation terminal 005 adds the interpretation information to the supplementary information of the displayed medical image according to inputs from the radiologist. The medical image observation terminal 005 also transmits the medical image, in which the interpretation information has been added to the supplementary information, to the medical image management device 002.

The interpretation report server 009 comprises a CPU and a memory area. The interpretation report server 009 stores the radio interpretation report transmitted from the interpretation report terminal 010 in its own memory area. The interpretation report server 009 also transmits a report UID for the stored interpretation report to the medical image storage unit 003 in order to register said report UID and an image UID for the medical image corresponding to said report in the database 008. A corresponding medical image as referred to herein is a medical image being linked to if said report has a hyperlink for the medical image. Additionally, if a JPEG image is placed on said report and a series UID or image UID is attached as the information corresponding to the JPEG image, the corresponding medical image is one that can be specified by that image UID, or image UID. This corresponding medical image is the "medical image added with specific information" of the present invention. Meanwhile, the interpretation report server 009 registers all of the image UIDs in the database 008 if a plurality of medical images are included in one report. A plurality of medical images that correspond to one report is hereinafter referred to as "related medical images."

After receiving a request to transmit the interpretation report according to an instruction from a requesting physician through the reference terminal 006, the interpretation report server 009 transmits the interpretation report to the reference terminal 006. The interpretation report server 009 also transmits the report UID and image UID to the medical image management device 002 according to an instruction from the requesting physician and then transmits to the medical image management device 002 an instruction to transmit the medical image that corresponds to that report UID and image UID.

The medical image management device 002 receives the report UID and image ID, as well as a request to transmit the medical image based on those UIDs, from the interpretation report terminal 010.

The medical image storage unit 003 transmits the medical image corresponding to the received image UID to the medical image observation terminal 005.

The evaluation management unit 004 comprises a CPU and a memory area and preliminarily records a table showing the creator names and the corresponding destinations for the evaluations.

After receiving the report UID and image UID from the interpretation report server 009, the evaluation management unit 004 instructs the reference terminal 006 to display a screen for entering the evaluation of the medical image transmitted from the medical image storage unit 003 corresponding to the interpretation report and image UID transmitted from the interpretation report server 009.

After receiving the input of the evaluation of the interpretation report from the reference terminal 006, the evaluation management unit 004 adds it to the supplementary information of the medical image that is related to said report stored in the database 008 of the medical image storage unit 003. As described herein, in this embodiment, the evaluation is added to the supplementary information of the medical image related to the evaluated report, but the evaluation may be added only to the supplementary information of the medical image displayed in the reference terminal 006.

Additionally, after receiving the inputs of the evaluation of the medical image displayed in the reference terminal 006 from the reference terminal 006, the evaluation management unit 004 adds said evaluation to the supplementary information of said medical image stored in the medical image storage unit 003.

As described herein, in this embodiment, the evaluation management unit 004 adds the evaluation itself to the supplementary information of the medical image. Conversely, rather than configuring the device to add the evaluation itself directly to the supplementary information, the evaluation management unit 004 can be configured to create a file of the evaluation that has been entered, store that file in a predetermined storage location, and add to the supplementary information of the medical image the information regarding the storage destination of that file.

Additionally, the evaluation management unit 004 can be placed within the interpretation report terminal 010 or the reference terminal 006. In this case, a report client or an image viewer on the interpretation terminal 010 or a HIS client on the reference terminal 006 will create the abovementioned evaluation file and add the storage destination thereof to the supplementary information of the medical image.

Moreover, the evaluation management unit 004 searches the database 008 of the medical image storage unit 003 for the name of the creator of the evaluated interpretation report in accordance with the interpretation report UID and image UID. The evaluation management unit 004 then refers to an internal table showing the creator names and the corresponding destinations for the evaluation in order to extract the destination for the evaluation corresponding to the creator being searched for.

The evaluation management unit 004 transmits the evaluation or the evaluation-related information, such as a storage destination, related to the interpretation report received from the reference terminal 006 and corresponding to the specific medical image to the extracted destination of the evaluation. Herein, when receiving the evaluation-related information such as a storage destination, an operator (e.g., a radiologist) can obtain the evaluation of the interpretation report they created by referring to the evaluation based on that information.

The reference terminal 006 is an information terminal comprising a CPU, examples of which include a PC (personal computer).

The reference terminal 006 sends a request to the medical image management device 002 for the medical image in accordance with the instruction of a requesting physician and displays the medical image received from the medical image management device 002.

Additionally, the reference terminal 006 displays the evaluation input screen that has been transmitted from the evaluation management unit 004.

The reference terminal 006 transmits the evaluation of the interpretation report to the evaluation management unit 004 in accordance with the input from the requesting physician.

[Third Embodiment]

The third embodiment of the present invention is a system in which a warning is reported if the evaluation of the interpretation information or the evaluation-related information is not transmitted after a specific period in an interpretation support system according to the first or second embodiment.

The evaluation management unit 004 preliminarily records a period of 1 month as a threshold.

The evaluation management unit 004 starts counting the time when the evaluation screen is displayed in the reference terminal 006. The evaluation management unit 004 then stops counting when the evaluation of the interpretation information or the evaluation-related information related to the displayed medical image is transmitted from the reference terminal 006.

The evaluation management unit 004 will transmit a warning stating that evaluation has not been performed and then instruct the reference terminal 006 to display the warning if the reference terminal 006 does not transmit the evaluation of the interpretation information or the evaluation-related information related to the displayed medical image after the time count exceeds one month.

As described herein, in this embodiment, the threshold is set as one month in consideration of the time required for a requesting physician as well as the urgency of evaluations of an interpretation for the radiologist. However, this period is not limited to this number and the threshold will preferably be changed depending on the operations of the interpretation support system.

Additionally, in this embodiment, a warning is displayed in the reference terminal 006, but this warning may also be displayed in the medical image observation terminal 005 in order to report to the radiologist that the evaluation has not been performed.

What is claimed is:

1. An interpretation support system, comprising:
   a medical images capturing device configured to obtain medical images from a patient;
   a medical image storage configured to store a medical image of the medical images obtained from the medical image capturing device and supplementary information attached to the medical image;
   a medical image observation terminal configured to receive from a creator and to add, to the supplementary information stored in the medical image storage, interpretation information comprising comments or annotations regarding said medical image obtained from the medical image capturing device, and a name of the creator of said interpretation information;
   a reference terminal configured to obtain the medical image from the medical image storage according to an instruction from an operator, and configured to enter an evaluation of the interpretation information, the evaluation providing feedback indicating satisfaction or not with the interpretation information to the creator; and
   a central processing unit implementing an evaluation management unit and configured to
   obtain the evaluation from the reference terminal,
   refer to the name of the creator added to the supplementary information to specify a destination for the evaluation,
   add the evaluation entered by the reference terminal to the supplementary information of the medical image stored in the medical image storage, and
   transmit a report including said evaluation to the destination for creator review of the evaluation.

2. An interpretation support system according to claim 1, wherein:
   the medical image observation terminal, in response to an input of a destination for the evaluation that corresponds to the creator name, configured to add said destination for the evaluation to the supplemental information of the stored medical image.

3. An interpretation support system according to claim 1, wherein:
   the central processing unit implementing the evaluation management unit is further configured to refer to a preliminarily recorded table showing creator names and destinations of the evaluation corresponding to the creator names, and to extract the destination of the evaluation based on the creator name added to the supplementary information of the medical image.

4. An interpretation support system according to claim 1, wherein
   the reference terminal is configured to display a warning if a preliminarily recorded specific period has passed within time since displaying the evaluation input screen in the reference terminal until time of receiving an input of the evaluation.

5. An interpretation support system according to claim 1, wherein
   the central processing unit implementing the evaluation management unit is further configured to transmit to the destination for the evaluation result information indicating that period has passed without receiving any input of the evaluation, if a preliminarily recorded specific period has passed within time since displaying the evaluation input screen in the reference terminal until time of receiving an input of the evaluation.

6. An interpretation support system according to claim 1, wherein
the destination of the evaluation is encrypted.

7. An interpretation support system according to claim 1, wherein
the central processing unit implementing the evaluation management unit is further configured to add to the supplementary information the evaluation and information for specifying a person who performed said evaluation.

8. The interpretation support system according to claim 1, wherein the medical image capturing device is one of an X-ray apparatus, a magnetic resonance imaging (MRI) apparatus, and positron emission tomography (PET) apparatus.

\* \* \* \* \*